(12) United States Patent
Johns

(10) Patent No.: US 7,367,737 B2
(45) Date of Patent: May 6, 2008

(54) PASTE-N-BRUSH

(75) Inventor: Brian D. Johns, Celina, OH (US)

(73) Assignee: Brian Johns, Celina, OH (US)

( * ) Notice: Subject to any disclaimer, the term of this patent is extended or adjusted under 35 U.S.C. 154(b) by 23 days.

(21) Appl. No.: 11/141,960

(22) Filed: Jun. 1, 2005

(65) Prior Publication Data
US 2006/0115317 A1 Jun. 1, 2006

Related U.S. Application Data

(63) Continuation of application No. 11/010,589, filed on Dec. 13, 2004.

(60) Provisional application No. 60/653,226, filed on Feb. 15, 2005, provisional application No. 60/634,507, filed on Nov. 29, 2004.

(51) Int. Cl.
*A46B 11/04* (2006.01)

(52) U.S. Cl. ............... 401/277; 401/174; 401/178; 401/179; 401/171

(58) Field of Classification Search ........ 401/171–182, 401/270, 277, 269, 278
See application file for complete search history.

(56) References Cited

U.S. PATENT DOCUMENTS

| | | | |
|---|---|---|---|
| 1,212,010 A * | 1/1917 | Brown | 401/278 |
| 1,899,984 A * | 3/1933 | Powell | 401/278 |
| 2,868,215 A | 1/1959 | Mechem | |
| 4,128,349 A * | 12/1978 | Del Bon | 401/176 |
| 4,521,128 A * | 6/1985 | O'Neal | 401/183 |
| 4,580,588 A | 4/1986 | Swope, Jr. | |
| 4,717,278 A | 1/1988 | Kemeny | |
| 4,733,983 A | 3/1988 | Hertrampf | |
| 4,753,373 A | 6/1988 | Seager | |
| 4,826,341 A | 5/1989 | Kwak | |
| 4,883,204 A * | 11/1989 | Kay et al. | 401/278 |
| 4,917,273 A | 4/1990 | Seager | |
| 5,346,324 A * | 9/1994 | Kuo | 401/176 |
| 5,382,106 A * | 1/1995 | Voigt | 401/175 |
| 5,636,933 A * | 6/1997 | Vizsolyi | 401/171 |
| 6,142,694 A | 11/2000 | Rivlin et al. | |
| 2002/0114658 A1* | 8/2002 | Allen et al. | 401/176 |
| 2004/0057773 A1* | 3/2004 | Gray | 401/277 |

FOREIGN PATENT DOCUMENTS

WO WO 93/17936 A1 * 9/1993

\* cited by examiner

*Primary Examiner*—Khoa D. Huynh

(57) ABSTRACT

A combination brush and dispenser apparatus for paste materials to be applied by brushing action, is provided as a brushing section with a first passage and portal leading to brush bristles and a matching dispensing section which supplies regulated amount of the material through a second passage into the first passage. The dispenser may optionally include a unitary apparatus with the two sections permanently attached, or a multi-section apparatus in which the brushing and dispensing sections are separable. Various forms of dispensing devices are described for controlling the quantity of paste material supplied to the brushing section for each separate use of the apparatus.

1 Claim, 20 Drawing Sheets

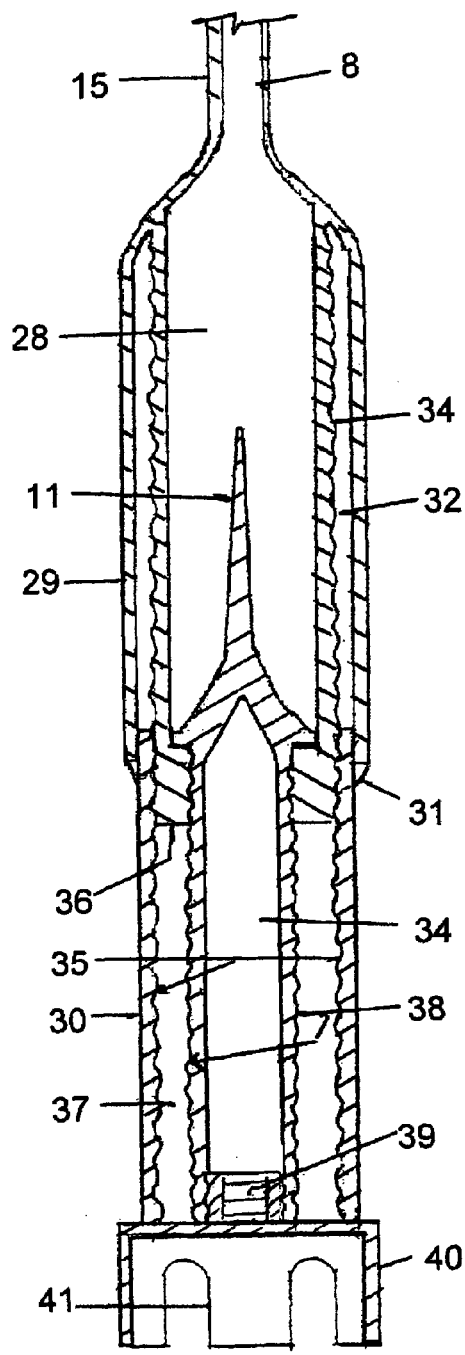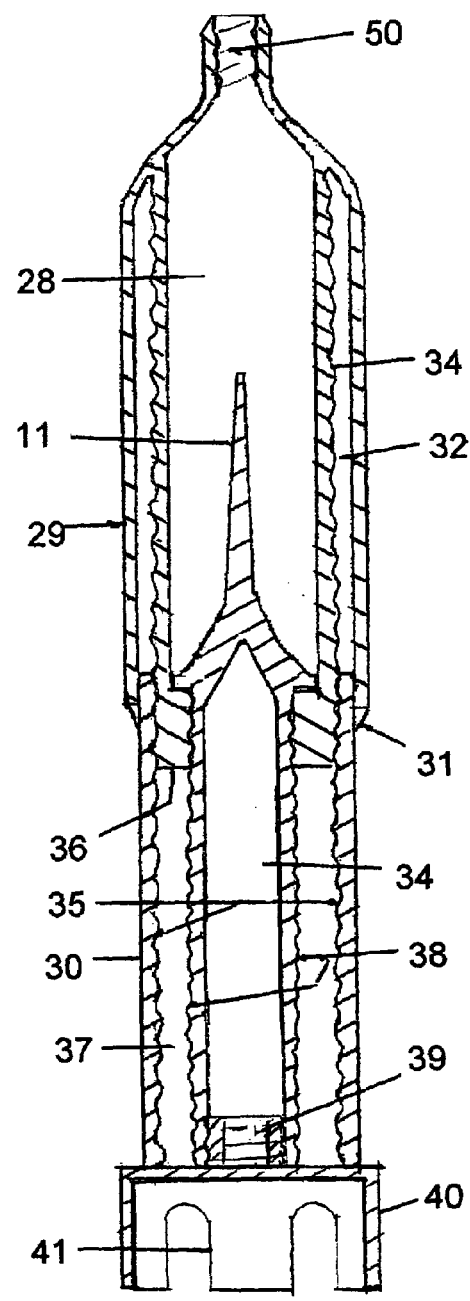
FIGURE 2C
FIGURE 4A

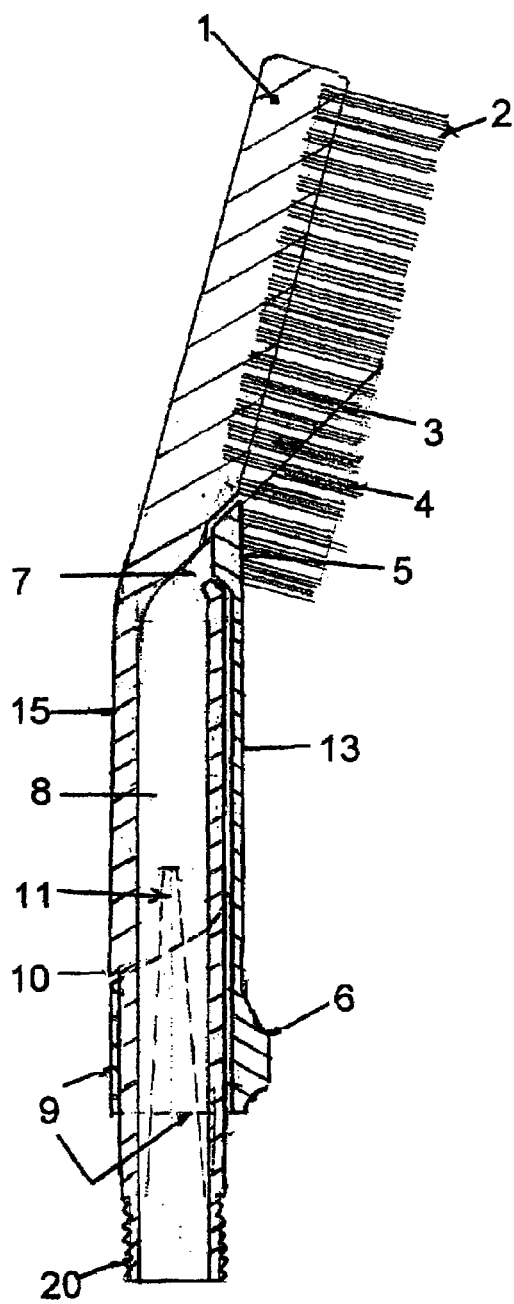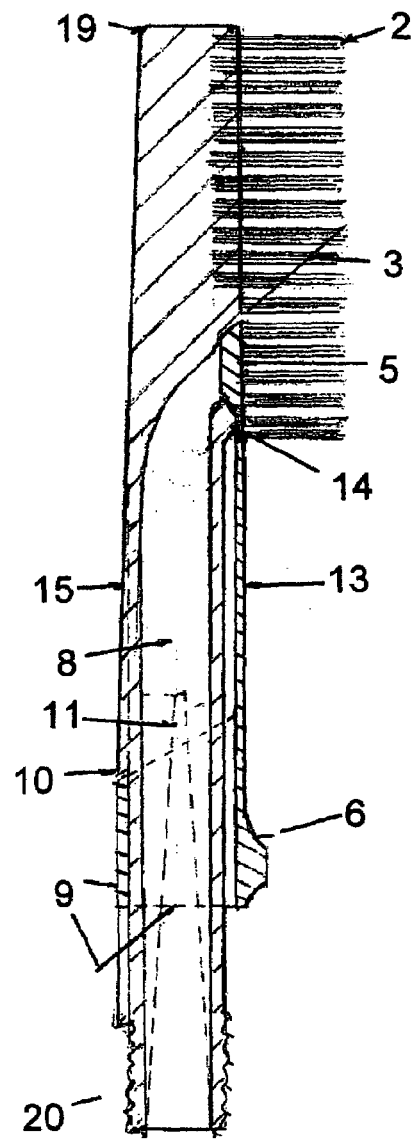
FIGURE 3C
FIGURE 3D

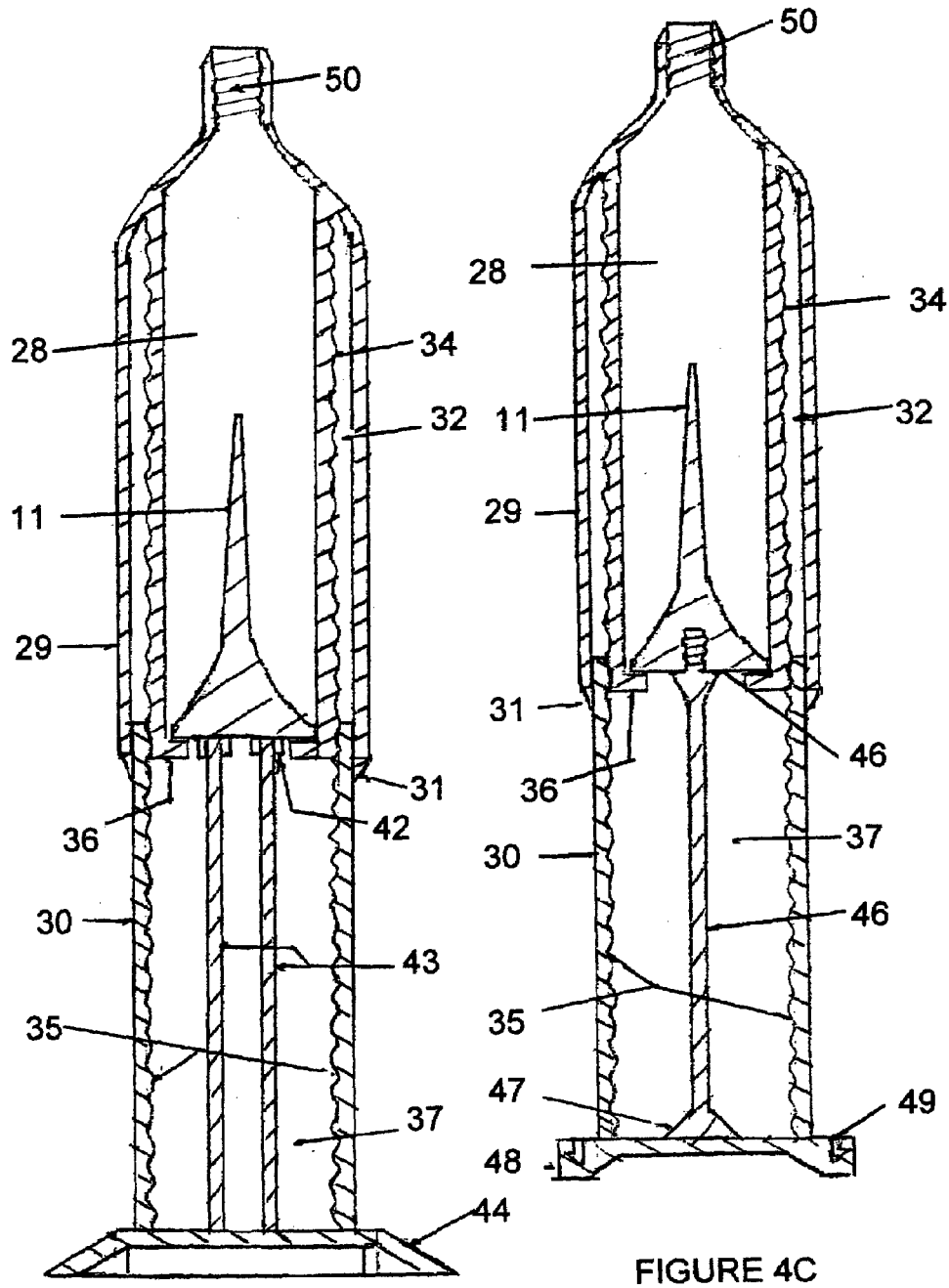

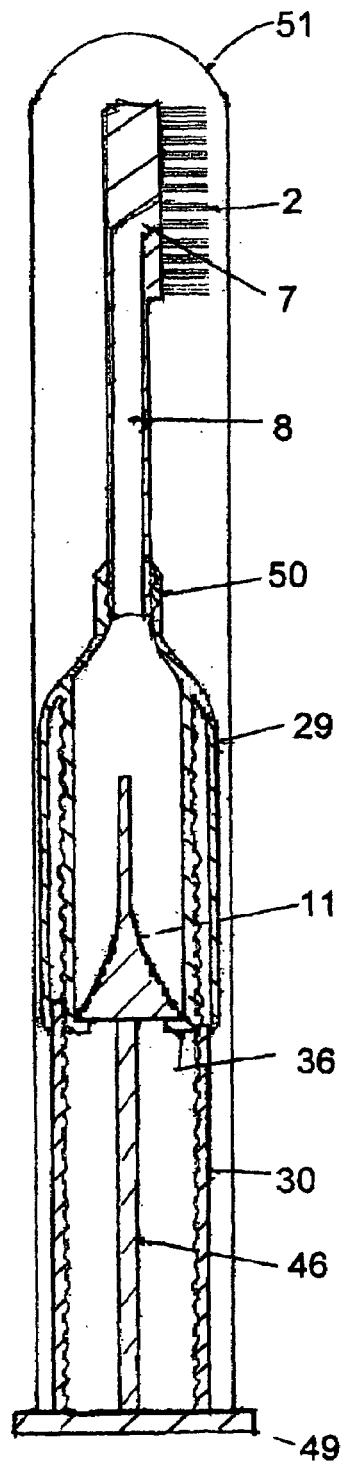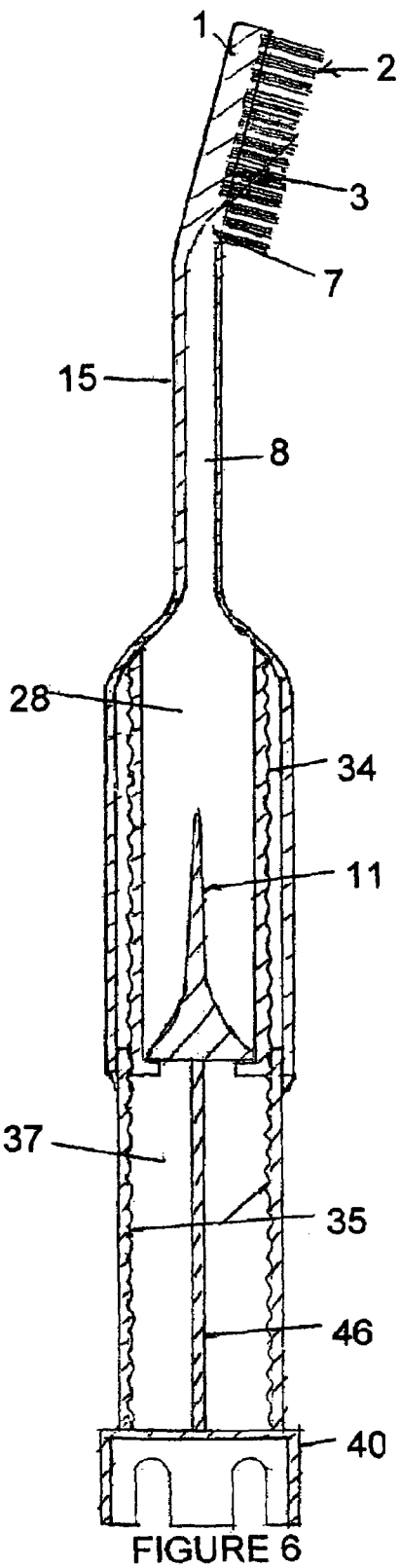
FIGURE 5
FIGURE 6

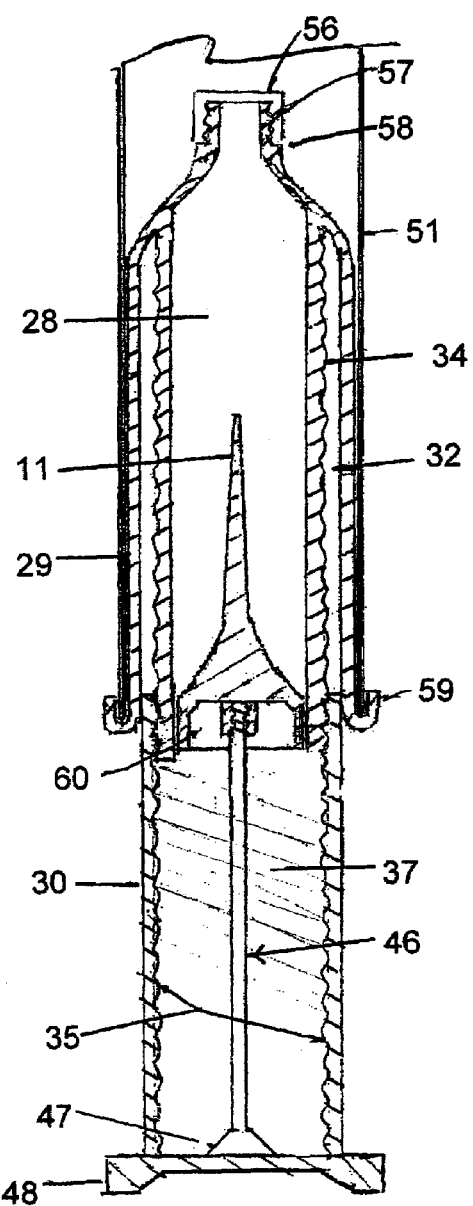
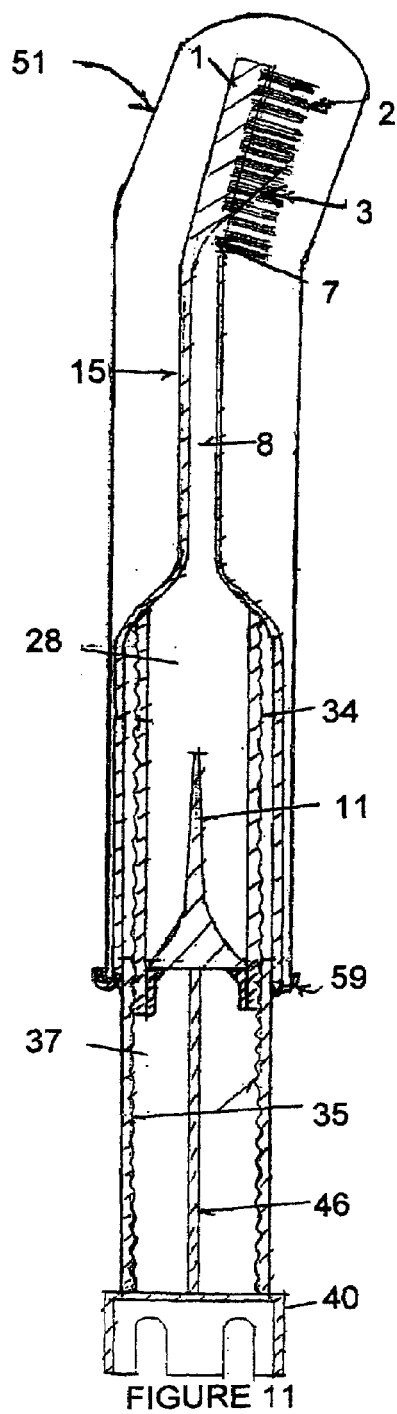
FIGURE 10
FIGURE 11

PASTE-N-BRUSH

RELATED APPLICATIONS

This application is a Continuation in Part of U.S. patent application Ser. No. 11/010,589 filed 13 Dec. 2004, and claims the benefit under 35 U.S.C. § 119(e) of U.S. Provisional Applications Ser. No. 60/634,507 filed 29 Nov. 2004 and Ser. No. 60/653,226 filed 15 Feb. 2005, the subject matter of each of which is hereby incorporated by reference.

FIELD OF THE INVENTION

The present invention relates to a combination toothbrush with toothpaste dispenser built in the unit. The invention may so be used to dispense any types of viscous liquids or paste that are in a flowable form. Basic applications for the Invention are for brushing teeth and dispensing toothpaste or gels, but is also intended for dispensing viscous paste materials such as medications, caulks, paints, foods and hygiene liquid products and similar products.

The Invention also is designed to be disposable as a whole assembly, as a unitary apparatus, or provided in two parts as an optionally disposable base and/or brush head replacement, either or both of which may be disposable or refillable. An important feature of the Invention is the use of a pointed plunge-type dispenser which enters a passage to the brush head and pushes a predetermined quantity of past-like material onto the bristles of the brush, and optionally, together with a tapered neck cavity in a brush section, into which the plunge-type dispenser can enter for the purpose of controlling and minimizing the dispensed amount of material.

SUMMARY OF THE INVENTION

This invention pertains to a manual brush with built in or attachable reservoir for paste or similar materials and can be designed to dispense the proper amount of paste with every use. The Invention is comprised of an upper brush section, including application bristles, and a lower dispensing (and measuring) section. In addition the Invention can be used and then disposed of and/or reused by means of replacement of base or replacement of toothbrush head or by refills from existing paste-like products. The dispensing section of the Invention includes a unique tapered pointed plunge dispenser which contributes to the uniform and precisely measured dispensing of paste material through a controlled port onto the bristles of the brush section.

BRIEF DESCRIPTION OF THE DRAWINGS

FIGS. 2A, 2B & 2C are vertical cross-sectional views of two forms of a paste storage & dispensing section which can be used with the various brush sections shown in FIGS. 1A-1F;

FIGS. 3A-3D are similar cross-sections of modifications of the brush sections, with the addition of threaded bottom ends for removable attachment to compatible paste storage and dispensing sections;

FIGS. 4A (sheet 5), 4B & 4C are vertical cross sections of additional paste storage & dispensing section having internally threaded necks for attaching to threaded bottom ends of brush sections as in FIGS. 3A-3D;

FIG. 5 is a vertical cross-section taken though an assembly of a lower storage and dispensing section, as in FIG. 4C, and an upper brush section, as in FIG. 3A or 3D, and including an optional cover for the brush section;

FIG. 6 is a vertical cross-section taken though an assembly of a lower storage and dispensing section, as in FIG. 4C, and an upper brush section, as in FIG. 1B or 3B;

FIGS. 10 & 11 are further vertical cross-sections of the dispensing section (FIG. 10) and the unitary assembly of brush and dispensing sections, showing details of the supports for a cover;

DESCRIPTION OF PREFERRED EMBODIMENTS

Figure 1A:
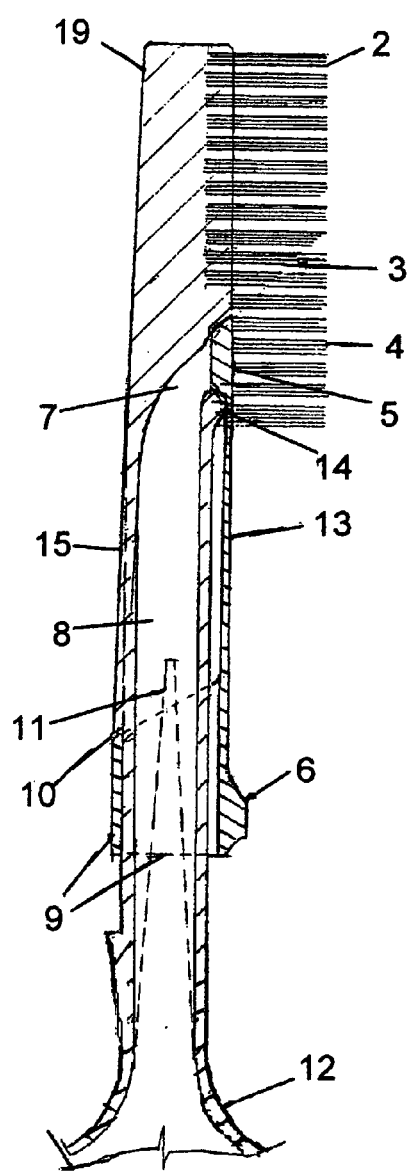
FIG. 1A is a vertical cross-section view of a vertical or straight brush section of one embodiment of the invention.

When turning the dispensing bases such a shown in FIGS. 2A through 2C and 4A through 4C, and FIGS. 3, 16 and 17 the toothpaste is moved through the shaft of the neck and onto to the toothbrush. All of the brush sections and dispensing sections can be disposable after the paste material is depleted from the dispensing section or when usage is no longer needed. Also, the dispensing sections such as in FIGS. 4B and 4C can be refillable with a regular tube of toothpaste or other such material by screwing an adapter 67 or 83 (FIG. 12A, or 12C) onto the top of the dispensing sections FIGS. 4B & C. The toothbrush head sections shown in FIGS. 3A through 3D and 9A can also be disposable after so many recommended uses.

The base of the Invention can be used as a unit that is purchased as one piece and disposable after paste is dispensed per FIGS. 4A, 4B, 4C, 5, 10, 13, 16 and 17

The body structures of all sections illustrated in the drawings can be made of suitable materials such as plastic, rubber or glass as a whole or part assembly.

Bristles may be made of nylon, plastic or other suitable standard manufacturer's material.

The size and shape of all the section embodiments may vary in height and diameter, for example taking into consideration the amount of paste material that one may wish to be stored in them. For example one may desire a unit which will be designed to supply paste-like material from under 7 days up to 30 or more days of usage before liquid is depleted from FIGS. 2A, 2B, 2C, 4A, 4B, 4C, 5, 6, 8, 10, 11, 13, 16, & 17 as a whole or part of an assembly.

Figure 1B:
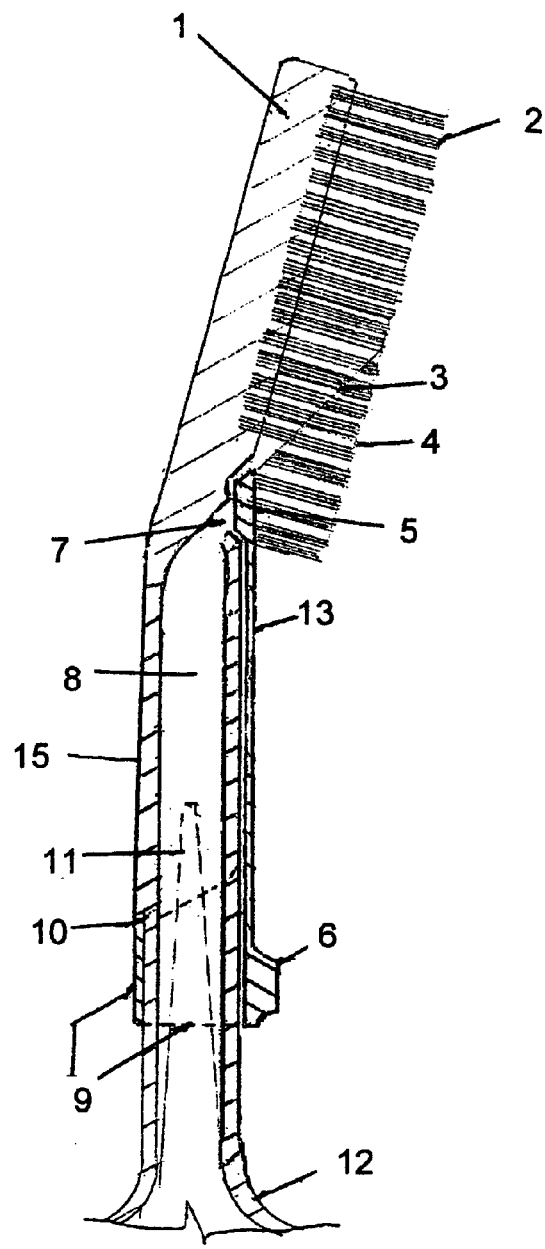
FIG. 1B is a vertical cross-section view of a tilted similar brush section of another embodiment.
Figure 1C:
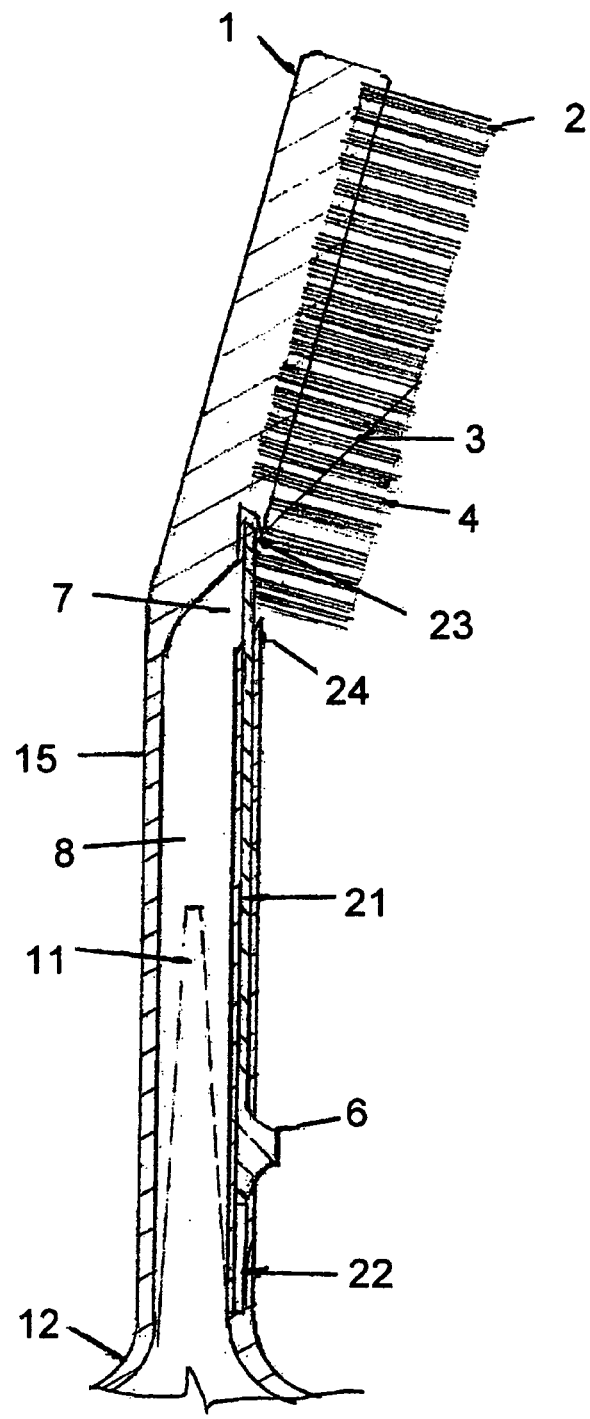
FIG. 1C is a view similar to FIG. 1A, with another form of port gate controlling the egress of paste into the brush section.
Figure 1D:
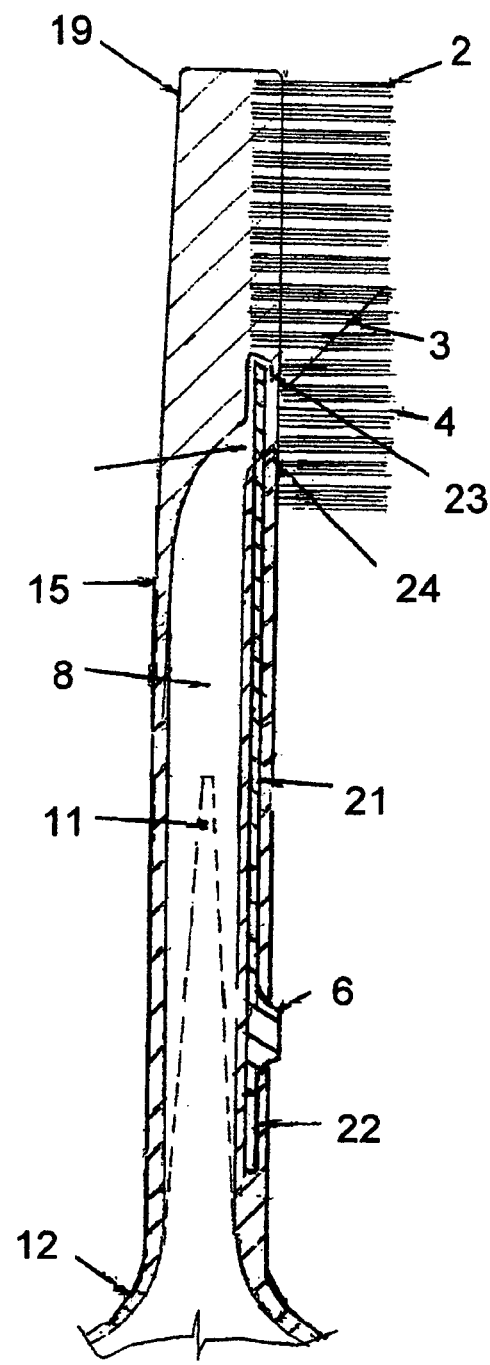
FIG. 1D is a view similar to FIG. 1B, with another form of port gate controlling the egress of paste into the brush section.
Figures 1E, 1F, 1G:
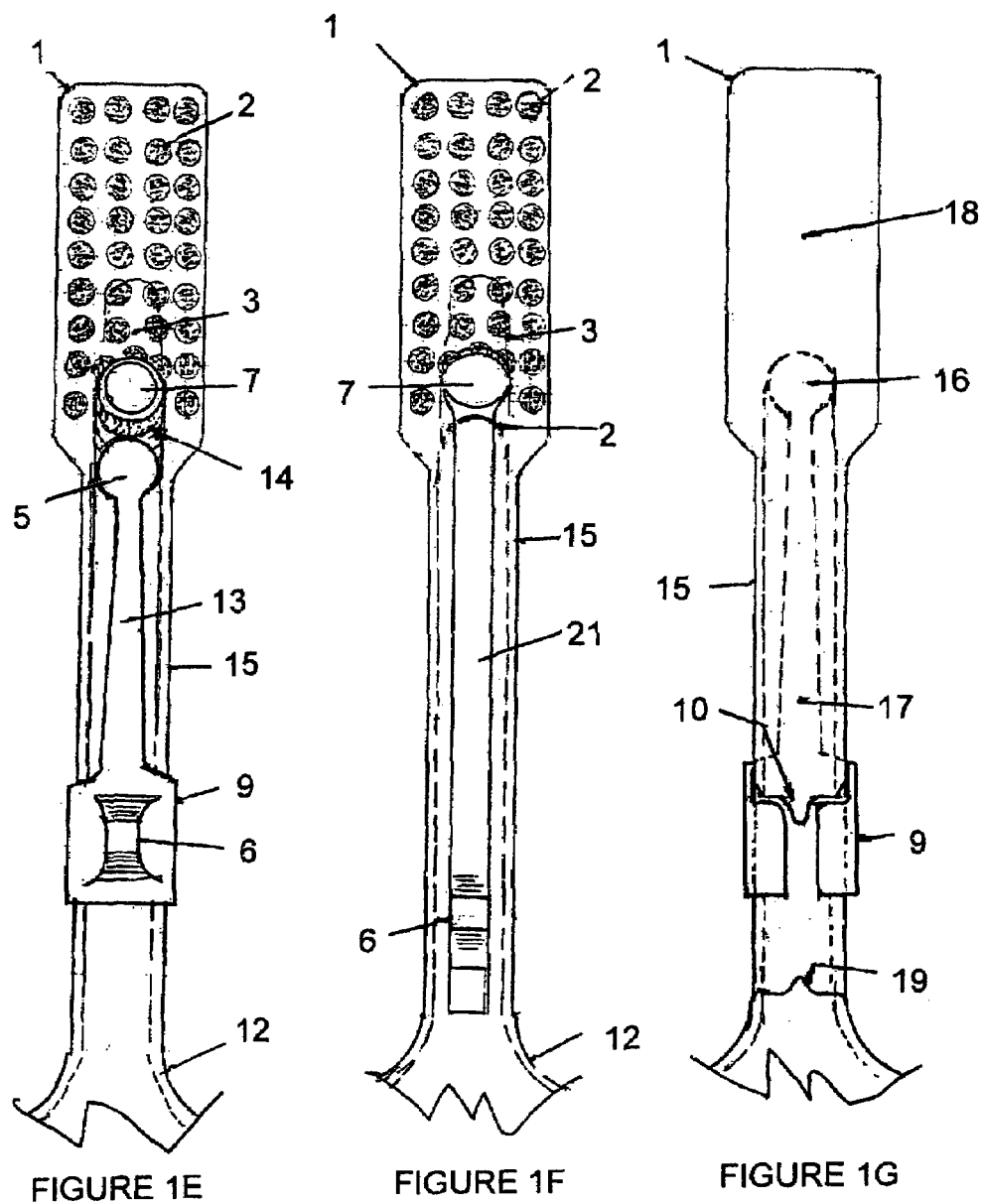
FIG. 1E is a frontal view of the brush section shown in FIGS. 1A & 1C.
FIG. 1F is a frontal view of the brush section shown in FIGS. 1B & 1D.
FIG. 1G is a rear view of the brush section shown in FIGS. 1A & 1C.

FIGS. 1A, 1B, 1C, 1D, 1E, 1F, and 1G illustrate two forms of a brush head (FIGS. 1A, 1D show straight brushes; FIGS. 1B, 1C & 9 are tilted) with two different open & close devices 6, 13, & 21 for dispensing toothpaste to the brush bristles 2 and 3. All of these Figures show generally the same purpose of dispensing toothpaste through a hollow neck shaft 5 and its passage 8.

Figure 2A:
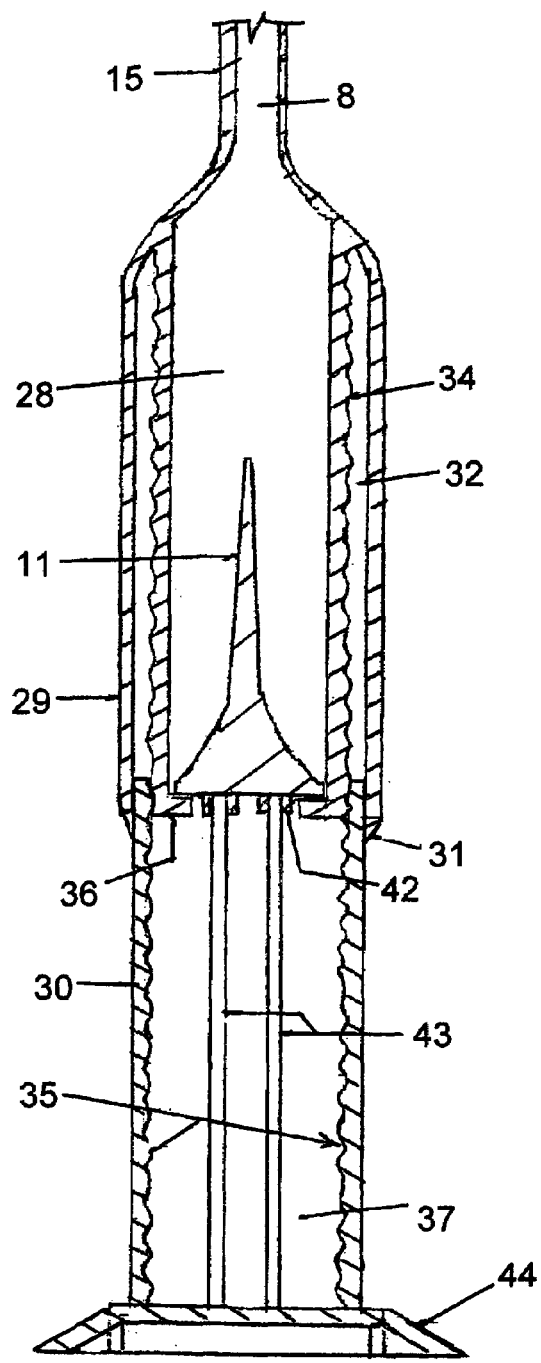
Figure 2B:
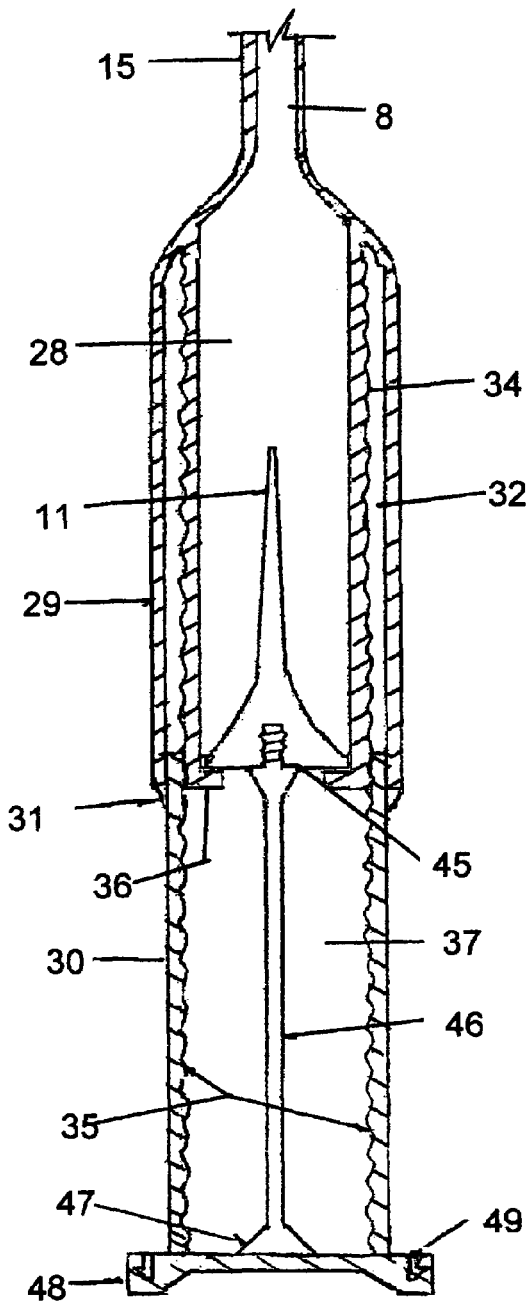

These FIGS. 1A through 1G can connect to dispensing sections as in FIGS. 2A through 2C as one unit; see FIG. 6. FIGS. 2A through 2C show the base or dispensing sections that stand up as shown in FIGS. 5,6,10 and 11.

The invention holds the paste material in sections cavities 28.

FIGS. 2A, 2B, 2C, 4A, 4B, 4C, 5, 6, 8, 10, 11, 13, 16 and 17, although specifically different from each other, all function in the same way by turning the base of the Figure clockwise or counter clockwise depending on the thread design.

A turn and lock mechanism (of known construction) can be incorporated in the dispensing sections that will let the threads lock when advancing, but which will not let the threads retract.

Seven different dispensing section base designs are disclosed, as well as five different ways to move the pointed plunge dispenser 11.

When turning the base of the dispensing mechanisms illustrated in FIGS. 2A, 2B, 2C, 4A, 4B, 4C, 5, 6, 8, 10, 11, 13, 16 and 17, the pointed plunge dispenser 11, which is common to the somewhat different units, will dispenses the toothpaste up the toothpaste neck shaft 15 as far as possible so very little toothpaste is left in the neck shaft, and is mostly fed out onto the bristles 2 and 3 of the brush section.

FIGS. 3A, 3B, 3C, 3D, 9A and 9B illustrate replaceable brush sections that screw and unscrew onto the top of the dispensing sections shown in FIGS. 4A, 4B, 4C, 10, 13, 16 and 17; see threaded necks 50 and 57.

The brush sections illustrated in FIGS. 3A, 3B, 3C, 3D, 9A and 9B also dispense paste material through the neck shaft 15 via its internal passage 8, and are similar to the brush sections illustrated in FIGS. 1A through 1G. FIG. 5 illustrates attaching (threading together) brush sections such as in FIGS. 3A through 3D and FIGS. 4A through 4C as a whole assembly.

FIGS. 4A through 4C are illustrations of dispensing sections that include a base 40, 44, & 49 which allow those sections to stand up. Cavities 28 (FIGS. 2A, 2B, 2C, 4A, 4B, 4C, 5, 6, 8, 10, 11, 13, 16 and 17) hold paste material and dispense toothpaste through the shaft necks 15 and out of portal hole 7 and onto the bristles 2 by turning the base of the assembly per FIGS. 5 and 6; see FIG. 5 for overall combined assembly Five different base designs are illustrated in FIGS. 4A through 4C, and all these bases can turn clockwise or counter clockwise depending on thread direction.

There are three different ways to move the pointed plunge dispenser 11, per FIGS. 4A through 4C. The pointed plunge dispenser moves up the shaft walls of cavity 28 and can move with the base while turning or can move straight up the shaft walls in one position while turning the base per FIGS. 13, 15 & 16. The pointed plunge dispenser 11 can be designed with a rubber seal located within the paste holder cavity 28 at the lower perimeter of the pointed plunge dispenser to keep liquids from dispensing into the base of the shaft 37.

FIGS. 5 and 11 show a plastic dome cover 51, over the entire assembly, which will protect the assembly when packaging or storing. Dome cover 51 may apply to all versions of the Invention (but is not required); see for example FIGS. 5, 10 and 11 which represent units ready for sale.

Dispensing the proper amount of the paste material will depend upon height and size of threads in relationship to the size and dimensions of a whole assembly, how many uses of the assembly are desired, e.g. a few applications of toothpaste per day compared to rapidly repeating applications of another paste material.

The outside of the dispensing sections, for example as shown in FIGS. 5, 6 and 11 can be provided with vertical lines that will line up with each other to inform a user how much paste material to dispense when turning the base to dispense paste material.

The finger operated open/close device 6 will allow a user to open and or close the portal hole 7 that dispenses paste material onto the bristles 2. The tapered bristle design, item 3 helps the toothpaste to start dispensing at the bottom of the toothbrush bristles then onto the bristle tops. Located at each side of the portal hole is a set of full size bristles that will hold the paste in place and act as a barrier wall when turning the base of the unit as a whole assembly and by natural gravity force will allow paste to reach the top of the bristle brushes. A portal hole 7 can be located anywhere within the head of the bristles (FIGS. 1E, 1F, & 1G) and be closed with an included manually operable plastic plug device 5 (optional) carried at the end of an arm 13. Arm 13 also is fitted with an operating tab 6 and is mounted within an external slide on the backside of neck 15, or with a C-shaped slide 9 which reaches partly around the neck.

Figures 7A, 7B, 7C, 8:
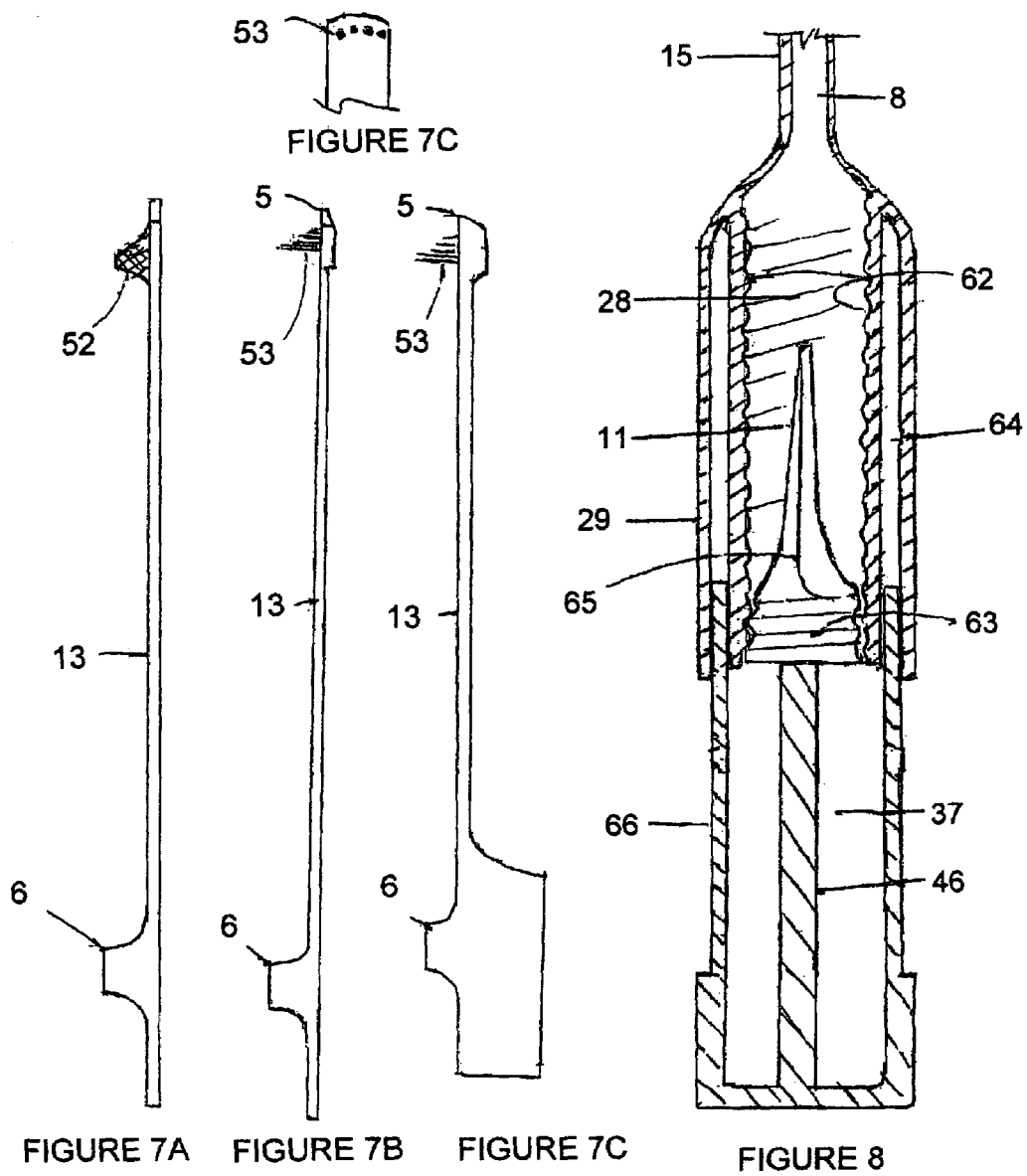
FIGS. 7A, 7B, & 7C are elevation views, from a side, of the fingers grips and open/close device for controlling ports into the bristles of brush sections.
FIG. 8 is vertical cross-section through another embodiment of dispensing apparatus.

FIGS. 7A, 7B and 7C illustrate the open close devices along with a small grouping of tapered bristles 52 and 53 which can function as a paste pusher and will push the paste up the tapered bristles and close the end of the brush head when the open close device is in a closed position.

FIGS. 7A, 7B and 7C show open close devices which can be used with FIGS. 1A, 1B, 1C, 1D, 3A, 3B, 3C, 3D, 9A and 9B as portal closures. FIG. 7D shows a paste pusher 53 located at the end of the open close device with full height straight line (or curved radius) bristles used that will close the end of the toothbrush head when the open close device is in a closed position. FIG. 7A, 7b and 7C, items 52 and 53 are not required for a working assembly in part or whole as shown in FIGS. 1A, 1B, 1C, 1D, 1E, 1F, 3A, 3B, 3C, 3D, 9A and 9B, but will help the paste go in the proper direction when closing portal hole 7.

FIG. 8 is a base assembly as whole and shows a threaded plunge dispenser 63 that will screw up into the cavity (toothpaste holder) 28 and will operate in the same manner as FIGS. 2A, 2B, 2C, 4A, 4B, 4C, 10, 13 and 16.

Per FIGS. 2A, 2B, 2C, 4A, 4B, 4C, 8, 10, 13 and 16, the pointed plunge dispenser can be attached to the bottom of the toothpaste dispenser base as a whole.

FIG. 8 shows at the bottom 66 of the dispensing section a threaded plunge dispenser 63, 65 These can be separate pieces per FIGS. 10, 4A, 4B and 4C.

Figure 9B:
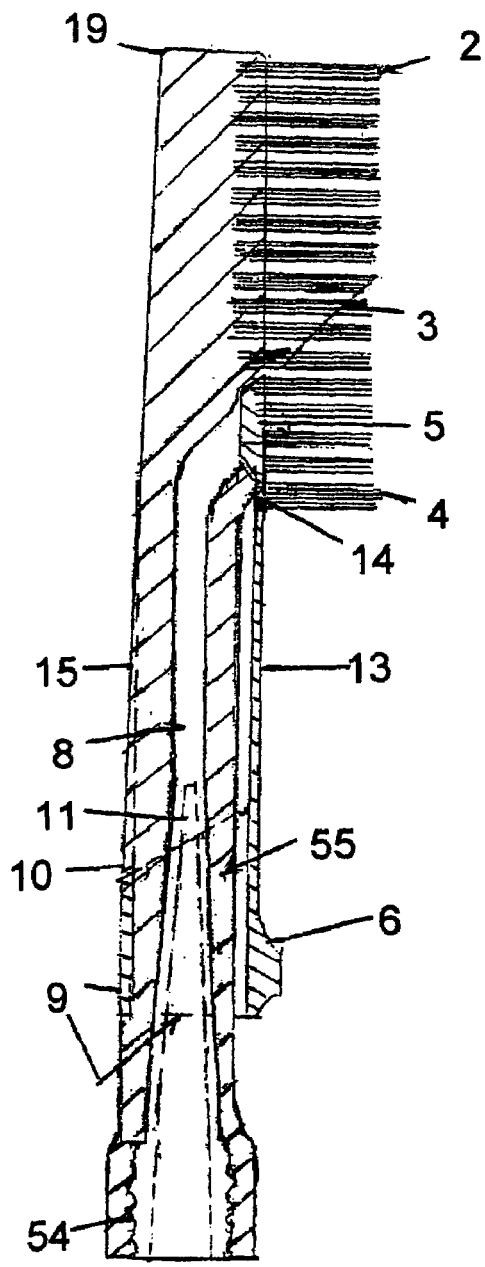
FIGS. 9A & 9B are vertical cross-sections taken though a brush section (as in FIGS. 3A & 3D)
Figure 9A:
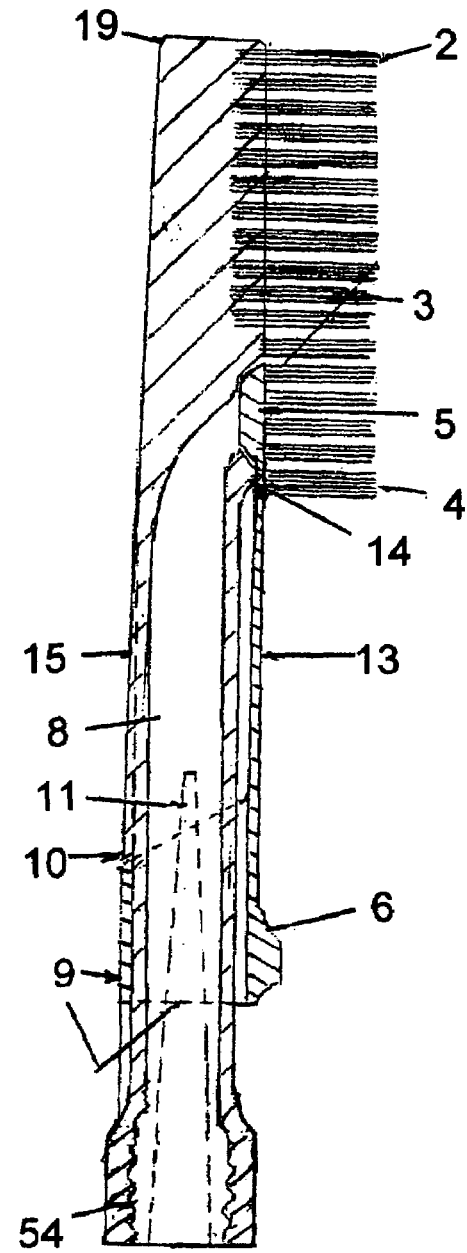

The brush head shown in FIG. 9A is similar to those shown in FIGS. 3C and 3D except the base of neck has internal threads 54 that will thread onto the neck 58 of the dispensing unit shown in FIG. 10 as a whole.

Figure 3A:
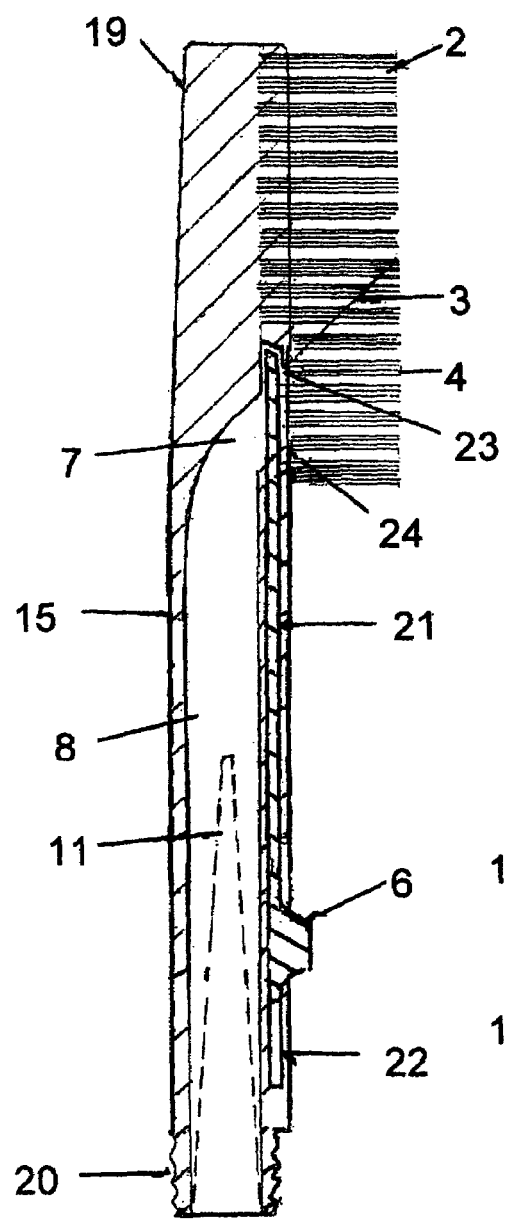
Figure 3B:
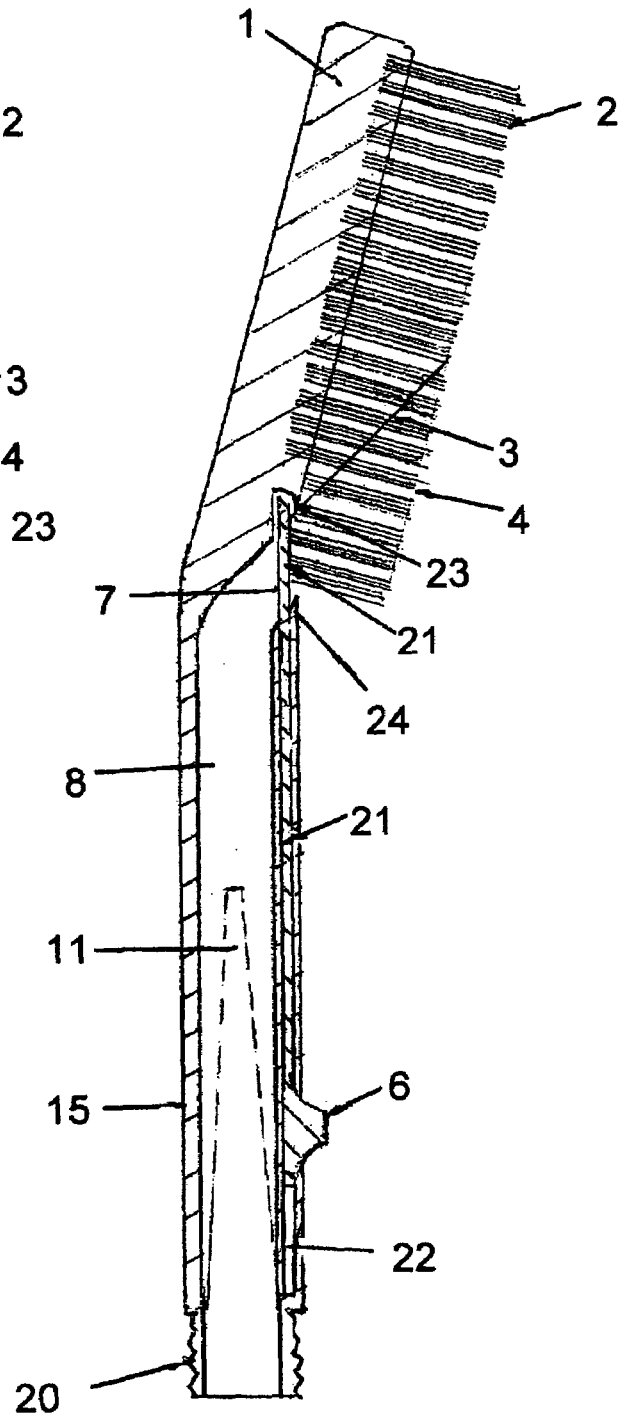

The brush section illustrated in FIG. 9B is similar to those shown in FIGS. 9A, 3C and 3D except the inside neck is tapered to conform to the shape of the pointed plunge dispenser 11, which will narrow the cavity passage 8 in shaft 15 and minimize waste of the paste material. Note that FIG. 9B includes an open/close device similar to FIGS. 3A and 3B, and has an internally threaded lower neck that will screw onto the top of the dispensing unit base shown in FIG. 10.

The exposed outer threads 57 can be closed with a plastic cap 56 and/or plastic dome cover 51. FIG. 10 also includes U-hook design 59 which will seat the plastic dome higher on the outer tube 30.

The hollow plunge dispenser base 60 will allow the plunge dispenser base to be deeper and higher and will eliminate the bottom stop 36 (see FIGS. 2A, B, C, & D and 4A, B & C).

FIG. 11 is a complete assembly of a tilted brush section and a dispensing section similar to FIG. 6 and fitted with a cover having an appropriately tilted upper end.

Figure 12A:
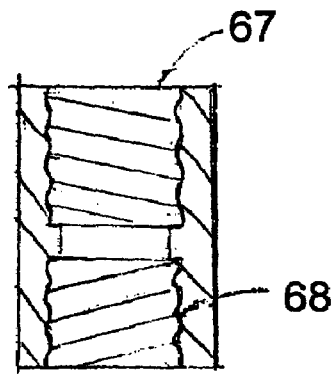
FIGS. 12A, 12B, 12C & 12D illustrate details of adaptors for engaging paste refill adaptors for use in renewing material supply in the dispensing sections.
Figure 12C:
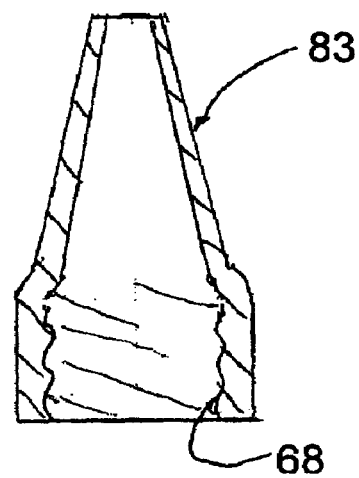
Figure 12B:
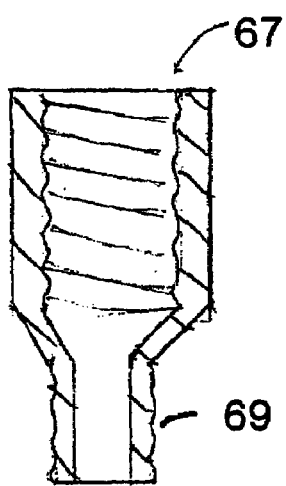

FIGS. 12A and 12B show universal adapters that will screw onto the tops of the dispensing sections shown in FIGS. 4A, 4B, 4C, 10, 13, 16 and 17 which will allow the dispensing section base unit to be refilled.

Figure 12D:
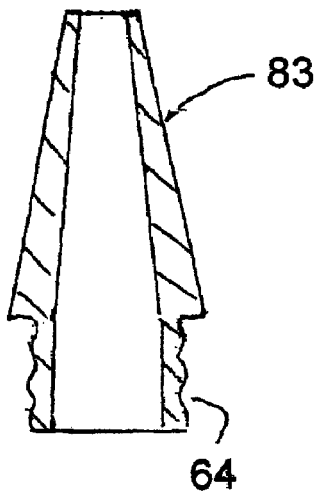

FIGS. 12C and 12D are universal adaptors that will screw onto the tops of FIGS. 4A, 4B, 4C, 10, 13, 16 and 17 which will to used to dispense all types of materials.

Figure 13:
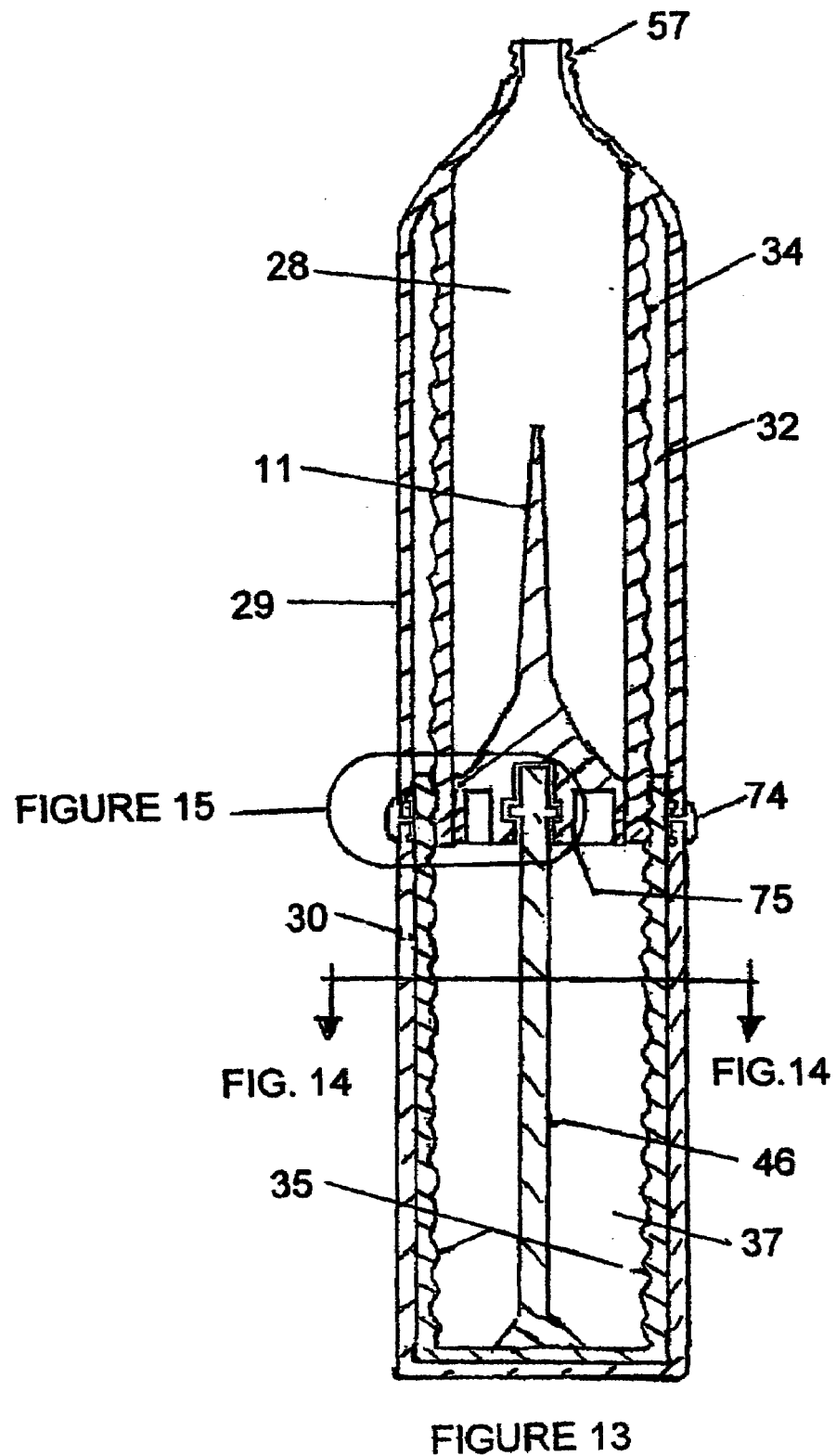
FIG. 13 illustrates a modified construction of a dispensing mechanism.
Figure 14A:
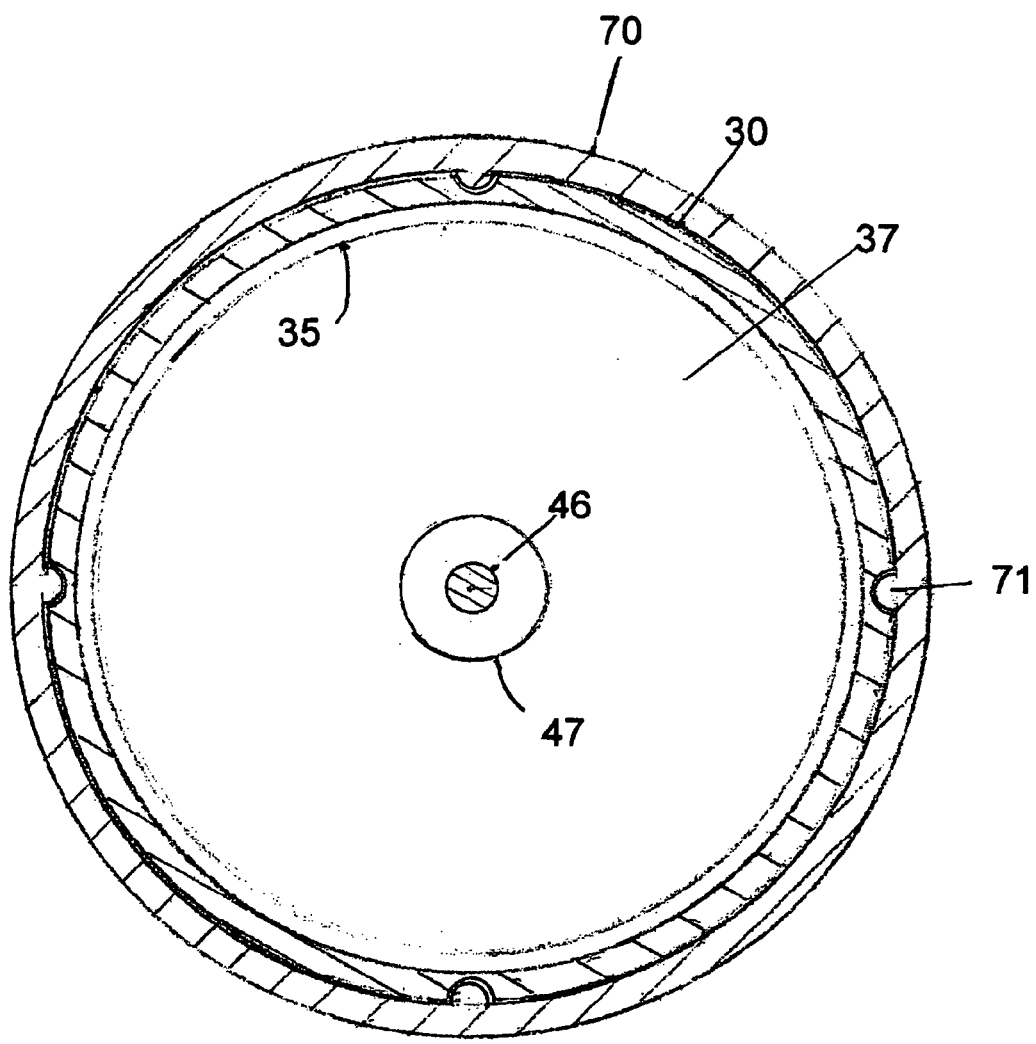
FIGS. 14A and 14B illustrate a horizontal cross-section of the embodiments of detent-type mechanisms allowing vertical motion of the plunge dispenser part without rotation, taken through section line 14-14 in FIG. 13.
Figure 14B:
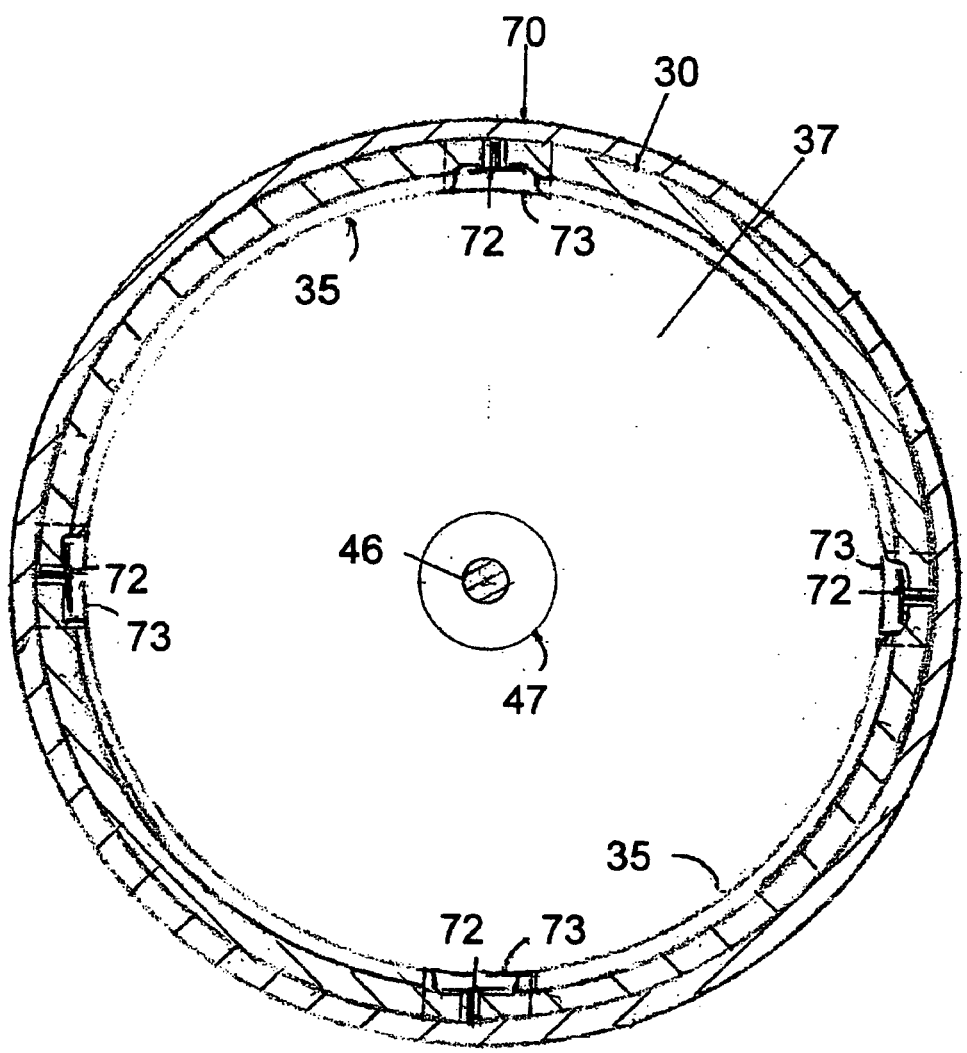

The embodiment of dispensing section shown in FIG. 13 is similar to those shown in FIGS. 4A, 4B, 4C and 10 except an outer plastic sleeve 70 has been added which will keep the figure the same size in length and keep the figure from shrinking in height. FIGS. 14A and 14B are cross-section views each taken though the region indicated on FIG. 13. Each shows one of two different designs which, by turning the base 30, will move the inner sleeve up into the upper assembly of the paste dispenser.

Figure 15:
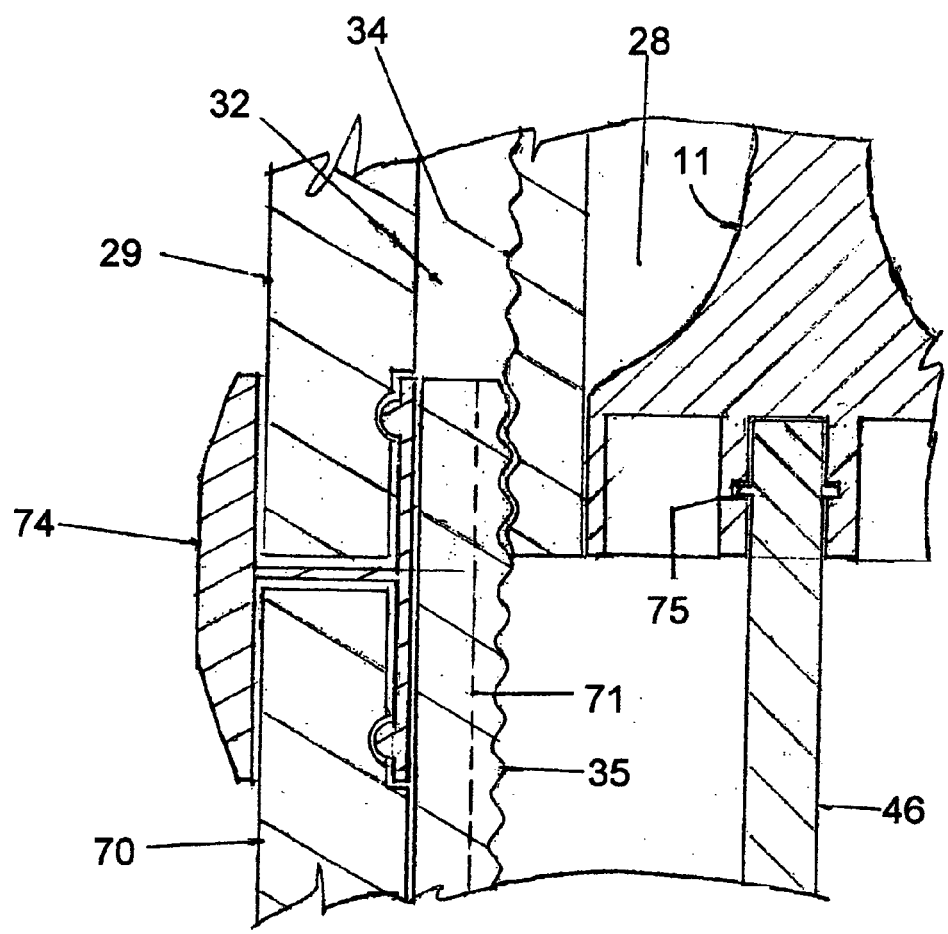
FIG. 15 is a partial enlargement of the detent and pusher mechanisms, taken in the region indicated on FIG. 13.

FIG. 15 is an enlarged partial cross-section of the outer perimeter rim 74 that holds the bottom outer sleeve 70 together with the exterior sleeve 29 of a paste dispenser. Turning the base of the assembly will allow the inner sleeve 30 to move up into the upper assembly 34, via the threads 34,35. The perimeter sleeve rim 74 will lock into the upper body assembly 29, while the lower outer sleeve 70 will slide around the backside rounded notch area of the sleeve rim while turning the outer sleeve Splines 71 (FIG. 14A) or splines 72 (FIG. 14B) will work in conjunction with the outer and inner sleeves, allowing the inner sleeve to move up into the upper body via hidden threads 34, 35 while turning the slip cover sleeve 70.

A continuous molded plastic ring 75 (on rod 46) slides within a slot located at the base of the pointed plunge dispenser 11, which allows the pointed plunge dispenser to move straight upward within the chamber 28.

Figure 16:
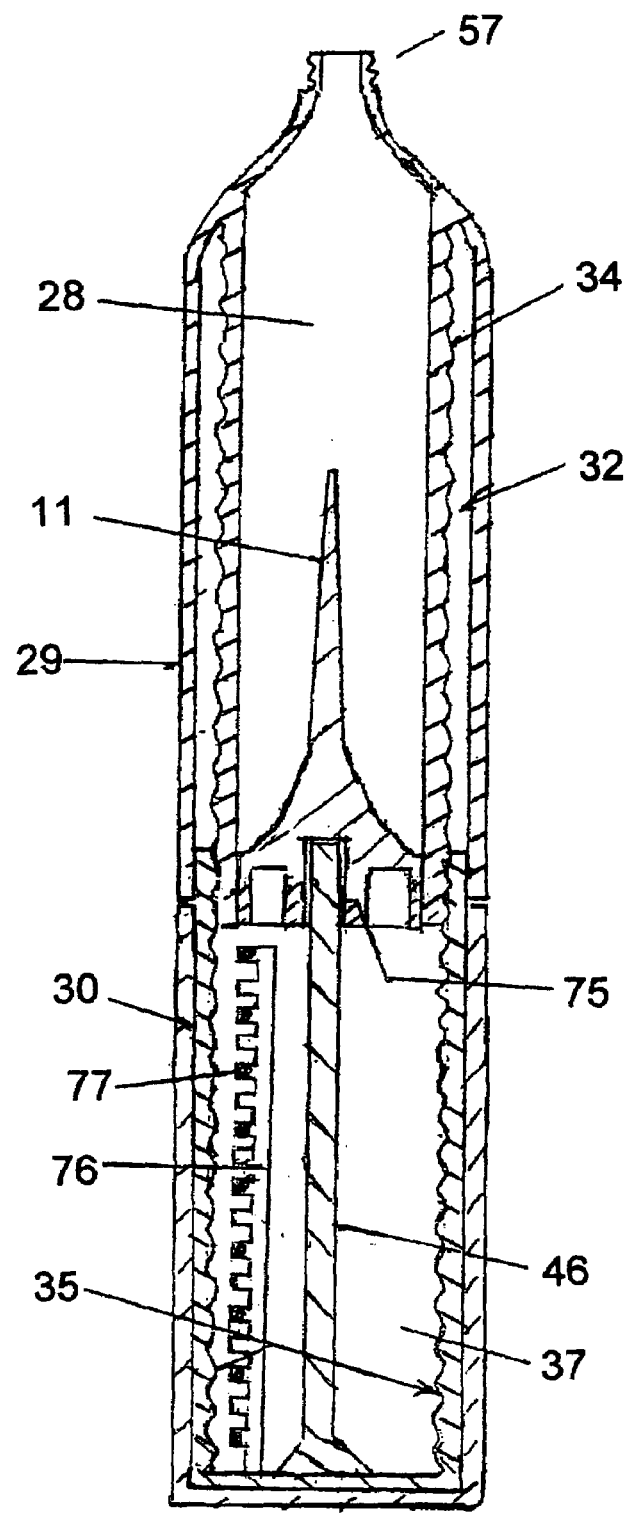
FIG. 16 is a vertical cross-section of anther embodiment of dispensing mechanism.

Referring to FIG. 16 shows a slip cover sleeve 70, that when separating from upper assembly and moving downward and away from the upper body assembly 29, and inserting to the next key lock by turning the outer sleeve with key stubs 77 into the vertical key lock 76 and away from the upper body assembly, then turning the slip cover sleeve 70, will move the inner sleeve upward into the upper body assembly item 29, top body toothpaste dispenser.

The vertical key lock 76 can be staggered down the inner sleeve instead of a vertical keyway and still produce the same function as in FIG. 16.

Figure 17:
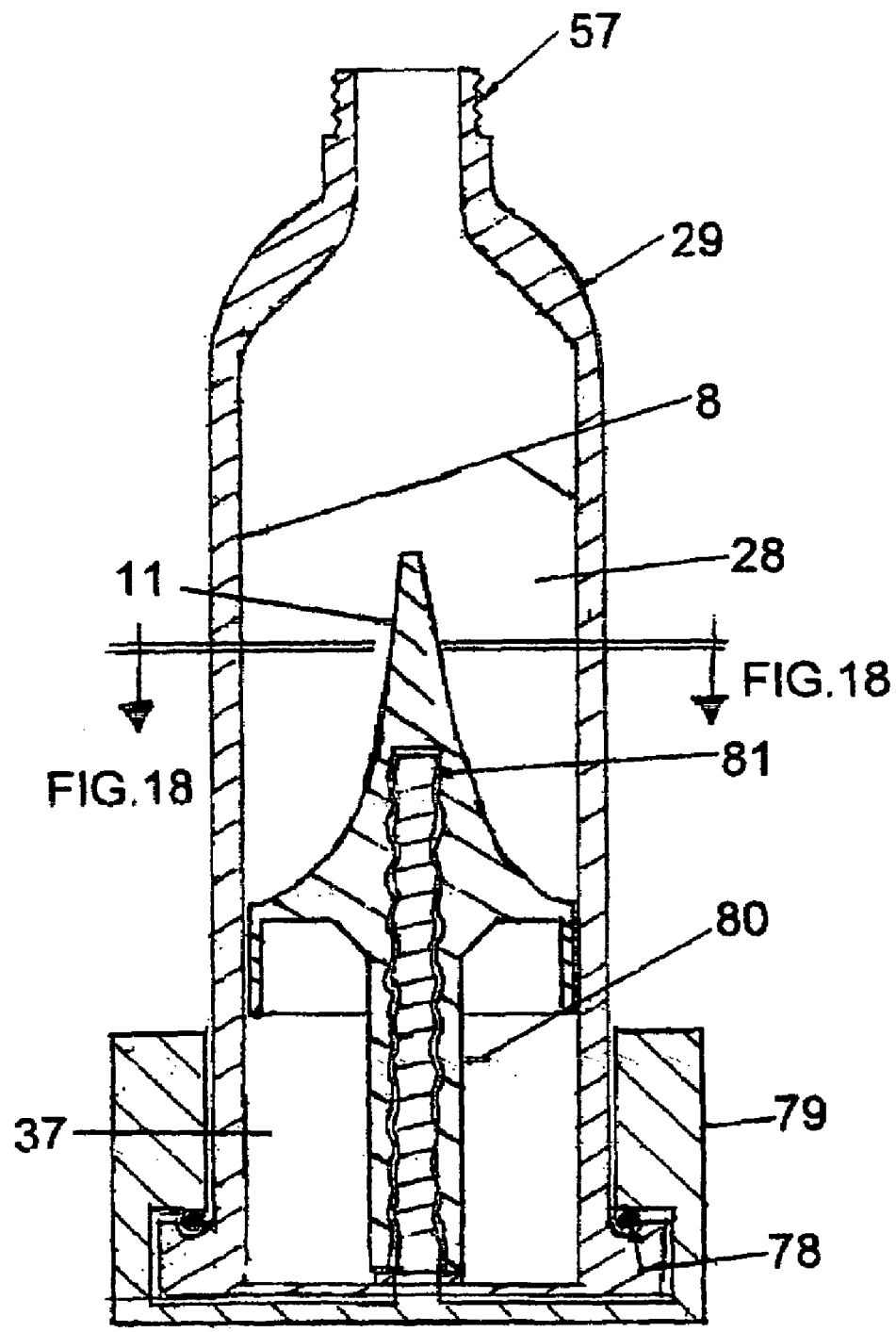
FIG. 17 is a foreshortened vertical cross-section of another embodiment of dispensing mechanism.

The construction shown in FIG. 17 works similarly to the embodiment shown in FIGS. 4A, 4B, and 4C except the paste dispenser base is no longer needed and paste material is concealed in one compartment.

When turning the base 79 in FIG. 17 the inner threaded shaft 81 will raise pointed plunge dispenser 80 upward around the inner threaded shaft 81. The diameter of inner threaded shaft 81 can be enlarged if there is need for greater leverage, and still operate the same.

FIG. 17 illustrates ball bearings 78 placed around of base so twist handle base 79 will turn easily and adequate pushing force will be transferred to the bearings 78.

Figure 18:
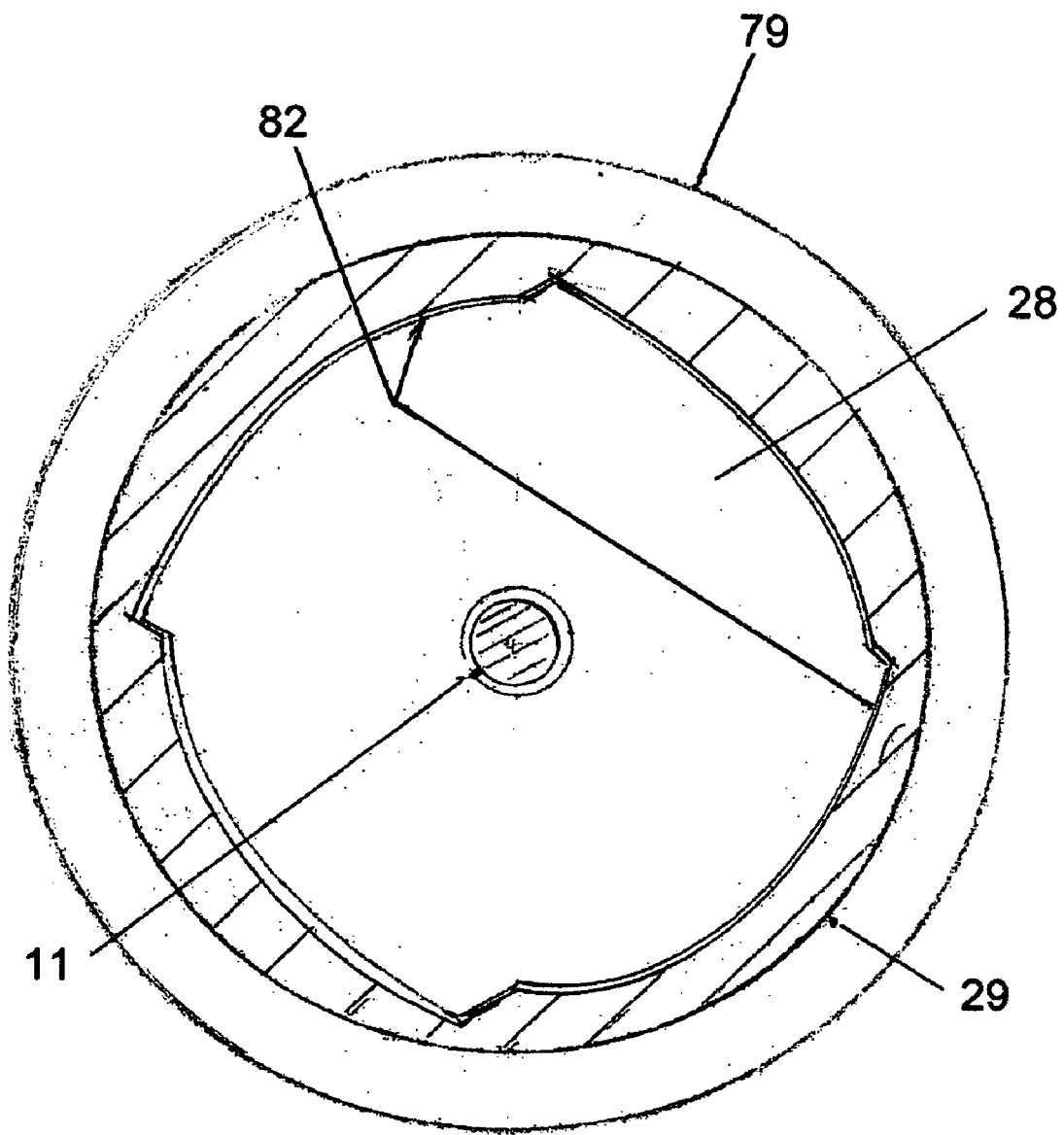
FIG. 18 is a horizontal cross-section through the lower portion paste dispenser area of FIG. 17.

FIG. 18 is the cross section view through FIG. 17 and shows the deformed circular shape of the plunge dispenser base and the interior wall 82 of the paste cavity that will keep the pointed plunge dispenser concentric with the threads as vertically. That cross sectional shape may be changed so long as the shape does not interfere with paste movement.

INDEX OF REFERENCE NUMBERS

1. Tapered Brush Head
2. Brush Bristles
3. Tapered Bristles
4. Bristles Beyond
5. Paste Stopper
6. Finger Open/Close device to allow the flow and stopping of paste when used.
7a. paste portal hole.
8. paste cavity shaft.
9a. Backside of finger open/close device.
10. The Backside of paste
11. Pointed plunge dispenser, dotted line represents cavity is empty; solid lines represent unused position.
12. Bottom of neck shaft.
13. Slide shaft
14. Raised mound for paste stopper.
15. paste neck.
16. paste stopper
18. Backside of brush head.
19. Straight brush head.
20a. Threaded bottom of neck shaft
22. slide track
23. notch area recessed in brush
24. tapered edge of slide track cavity
27. slide shaft in an open position
28. paste cavity holder
29. top of body paste dispenser.
30a. body paste base
30c. A click and lock device
31a. tapered base edge
32. Threaded hidden cavity
34. hidden threads located within item 32
35. threaded inside cavity in item 30 bottom
36a. Bottom stop
37. air cavity at base of item 30
39. base screw that will screw into item 38
40a. standing base
40b. rough exterior skin or groove lines 41a. grooved arches
42a. hole inserts
42b. Hole inserts
43. straight shafts insert into item 42
44. tapered base
45a. treaded invert into item 11
46. tapered single shaft
47. tapered base
48. straight round base.
49a. grooved insert
49b. dome
50. tapered inverted threads
51. Dome cover
52. paste pusher
53. Tapered bristle paste pusher
53c. Rounded full height bristles
55. Taper and thickened inside neck wall
56. Screw on plastic cap top
57. Exposed outer threads
58. Rim ledge
59. Outer U-hook design
60. Hollow plunge dispenser base
61. Universal adapter
62. Inside threaded walls
63. Threaded plunge dispenser
64. Smooth inside shaft wall
65. Swirl design
66. Bottom of body paste base
67. Top end of adaptor
68. Bottom end of FIG. 12A
69. Bottom end of FIG. 12B
70. slip cover sleeve
71. Slip cover sleeve notch
72. Plastic Tee molded with item 70
73. Notched base of inner sleeve
74. Perimeter sleeve rim
75. Perimeter slide notch
76. Key lock
77. Key stubs
78. Ball bearing base
79. Twist handle base
80. raised and threaded base
81. Inner treaded shaft
82. Inner wall of paste cavity holder.

The invention claimed is:

1. A brush with integrated paste supply, said brush comprising:

an elongated brush head, said elongated brush head having a first surface and a second opposite surface, said second opposite surface having an upper portion and a lower portion, a plurality of bristles (2,4) extending upwardly from said upper and lower portions of said second opposite surface of said elongated brush head, said elongated brush head further having a paste portal hole (7) formed at said lower portion of said second opposite surface of said elongated brush head, a plurality of tapered bristles (3) extended upwardly from said lower portion of said elongated brush head and formed around said paste portal hole, wherein said plurality of bristles (4) surrounding said plurality of tapered bristles at said lower portion of said elongated brush head, said elongated brush head further having a paste neck (15) and a bottom neck shaft (12), said paste neck defining an elongated paste cavity shaft (8) that connects said paste portal hole to said bottom neck shaft, a notch (23) recessed in said lower portion adjacent said paste portal hole, an open/close device mounted along said paste neck, said open/close device having a slide shaft, a finger engaging portion (6) and a paste stopper (5), wherein said paste stopper engaged said notch (23) and closed said paste portal hole (7) when said open/close device is not in use, and a paste supply holder having an upper end connected to said paste neck (15), a body (29), an inner casing having outer threads (34), wherein said body and said outer threads separated by a hidden cavity (32), said inner casing defining a paste cavity holder (28) containing a paste, a pointed plunge dispenser (11) disposed inside said paste cavity holder, said pointed plunge dispenser having a pointed top end and a wide base end fitting securely within said paste cavity holder, said paste supply holder further having a lower end connected to said upper end, said lower end and upper end connected to one another using a fastening mechanism, said lower end having a slip cover sleeve (70) encasing a body paste base (30), said body paste base having inner threads (35) and is slidably received in said hidden cavity (32), a rotatable shaft disposed inside said body paste base, said rotatable shaft having a top attached to said wide base of said pointed plunge dispenser, said slip cover sleeve (70) further having a plurality of protrusions formed on the inner surface, wherein said plurality of protrusions mated with a plurality of recesses formed on the outer surface of said body paste base (30), wherein said body (29) is flushed with said slip cover sleeve (70) when said lower end and upper end connected to one another, wherein upon manual rotation of said slip cover sleeve, the combination of said plurality of protrusions and recessed moves said body paste base into said hidden cavity (32), said inner threads (35) engaged outer threads (32) allowing said body paste base (30) to move upwardly along said hidden cavity and as the same time force said shaft and said pointed plunge dispenser (11) upwardly along said paste cavity holder (28) to push the paste into said elongated paste cavity shaft toward said paste portal hole, and wherein upon further manual activation of said open/close device, the paste is then ejected out said paste portal hole and onto said plurality of tapered bristles (3) and bristles (2,4).

* * * * *